US010405911B2

(12) United States Patent
Ferreira et al.

(10) Patent No.: US 10,405,911 B2
(45) Date of Patent: Sep. 10, 2019

(54) LONG STEM IMPLANT EXTRACTION TOOL

(71) Applicant: THE UNIVERSITY OF WESTERN ONTARIO, London (CA)

(72) Inventors: Louis Ferreira, London (CA); Joshua Eagen, London (CA); Dylan Murray, Roslin (CA); Emily West, Georgetown (CA); Jason Gharibo, Brampton (CA)

(73) Assignees: Louis Ferreira, London (CA); Dylan Murray, Roslin (CA); Joshua Eagen, London (CA); Emily West, London (CA); Jason Gharibo, London (CA)

( * ) Notice: Subject to any disclaimer, the term of this patent is extended or adjusted under 35 U.S.C. 154(b) by 418 days.

(21) Appl. No.: 15/075,684

(22) Filed: Mar. 21, 2016

(65) Prior Publication Data

US 2016/0270836 A1    Sep. 22, 2016

Related U.S. Application Data

(60) Provisional application No. 62/135,375, filed on Mar. 19, 2015.

(51) Int. Cl.
*A61B 17/92* (2006.01)
*A61F 2/46* (2006.01)
*A61F 2/30* (2006.01)

(52) U.S. Cl.
CPC .......... *A61B 17/921* (2013.01); *A61F 2/4603* (2013.01); *A61F 2/4612* (2013.01);
(Continued)

(58) Field of Classification Search
CPC ..... A61B 17/92; A61B 17/921; A61F 2/4603; A61F 2/4607; A61F 2/4612; A61F 2002/4636
See application file for complete search history.

(56) References Cited

U.S. PATENT DOCUMENTS 4,686,971 A * 8/1987 Harris ................... A61F 2/4607
606/99
5,045,054 A    9/1991 Hood et al.
(Continued)

FOREIGN PATENT DOCUMENTS

WO    2013134692    9/2013

*Primary Examiner* — Matthew J Lawson
(74) *Attorney, Agent, or Firm* — Hill & Schumacher

(57) ABSTRACT

The present disclosure provides an implant extraction tool for removing either cemented or non-cemented intramedullary stem implants from bones. The tool includes an elongated handle section having proximal and distal end sections with a cap section affixed to the distal end section of the elongated handle section, and cap section has a hole extending therethrough. The tool includes an attachment member having opposed ends, one of these opposed ends is configured to grip a cemented or non-cemented intramedullary implant stem in a bone. The attachment member has a size and shape to be received into the hole and the other of opposed end includes at least one hook feature for gripping the implant. The tool includes an elongated lever having an elongate proximal section and a shorter distal end section with a pivot fulcrum at a transition from the distal end section to the elongate proximal section. The distal end section is configured to engage the hook feature of the attachment when proximal end sections of the elongated handle section and the elongated lever are squeezed towards each other such that upon squeezing the attachment member is levered out of the hole in the cap section to effect removal of the stem implant.

9 Claims, 2 Drawing Sheets

(52) U.S. Cl.
CPC ............... *A61F 2002/30507* (2013.01); *A61F 2002/4619* (2013.01); *A61F 2002/4628* (2013.01); *A61F 2002/4629* (2013.01); *A61F 2002/4631* (2013.01)

(56) References Cited

U.S. PATENT DOCUMENTS

| | | | |
|---|---|---|---|
| 5,064,427 A * | 11/1991 | Burkinshaw | A61F 2/4612 606/99 |
| 5,290,291 A | 3/1994 | Linden | |
| 5,534,006 A * | 7/1996 | Szabo | A61F 2/4607 606/100 |
| 5,743,910 A * | 4/1998 | Bays | A61F 2/4607 606/99 |
| 6,193,725 B1 * | 2/2001 | Macey | A61B 17/921 606/104 |
| 8,486,084 B2 | 7/2013 | Huene | |
| 2004/0015238 A1 * | 1/2004 | Buehler | A61B 17/8808 623/22.12 |
| 2005/0203539 A1 * | 9/2005 | Grimm | A61F 2/4607 606/99 |
| 2008/0275457 A1 * | 11/2008 | Meek | A61F 2/38 606/99 |
| 2013/0261626 A1 | 10/2013 | Chavarria et al. | |
| 2014/0276883 A1 * | 9/2014 | Matyas | A61B 17/921 606/99 |
| 2015/0202056 A1 * | 7/2015 | Matyas | A61F 2/389 623/20.32 |

* cited by examiner

LONG STEM IMPLANT EXTRACTION TOOL

FIELD

The current disclosure relates to an implant extraction tool for removing either cemented or non-cemented intramedullary stem implants from bones.

BACKGROUND

Stemmed joint implants are used as a treatment for many problems, including osteoarthritis, torn rotator cuffs, severe fractures and pain. However, most implants only have a useful life of approximately ten to fifteen years, at which point, they must be removed and replaced. Sometimes, implants are replaced due to loosening, failure, or infection. The surgical tools currently used for the removal procedure are barbaric and the surgery often results in unintended damage to the surrounding bone and soft tissue from using these tools, which translates to longer time in surgery, a longer recovery time and a higher risk of infection.

Joint replacement, involving insertion of an orthopedic implant or prosthesis, is a common treatment for severe pain caused by osteoarthritis, severe fracture, or a torn rotator cuff. With an aging population, such joint replacement surgeries are increasingly common. In some cases, the original implant must be removed for replacement. Long stemmed implants that are cemented into the bone canal must be broken away from the cement in order to achieve removal. In the case of non-cemented implants, there is often some bone integration with the implant stem's surface, and this fixation must also be broken to remove the implant. If existing methods are not successful, then the patient's bone must be split open to gain access to the implant. This causes increased trauma and risk of complications, as well as prolonging the procedure and additional hospital stay. A reliable atraumatic method for removing the intramedullary stem component of an artificial joint implant is required.

A slaphammer is often used. Although its uses are not restricted to orthopedic surgery, a patent for a surgical slaphammer was filed in 2010 by Donald Huene. (U.S. Pat. No. 8,486,084, which can be found at http://www.google-.com/patents/US8486084). A slaphammer is a device that attaches to the extractor/inserter of the implant stem, has a weighted grip and can be used to pull vertically on the implant. The weight is slid up to a hard stop which transfers the momentum of the weight to the implant, and this impact is intended to break the cement fixation and dislodge the implant stem from the bone. Unfortunately, this method is often inadequate to break the cement bond. From here, surgeons have a number of other techniques they can use, each with their own pitfalls.

A commonly used method at the surgeons' disposal is the disimpaction technique. In this technique, osteotomes are inserted along the implant-bone interface with the intention of disrupting the implant's circumferential fixation. This process requires removing bone and cement from around the collar of the prosthesis, exposing the underside and allowing space for a round or square bone tamp. From here, the stem can be malleted out in a retrograde fashion. Flexible (versus rigid) osteotomes can be used when initially disrupting the implant fixation to reduce the number of cortical perforations. Still, this is not a guaranteed method and a wide entry point needs to be created for placement of bone tamps which is difficult to create and not ideal.

Another drawback is that the removal of so much bone can be costly, potentially requiring the need to allograft bone to build up the available bone stock, requiring further healing time. Due to the high impact energies generated during removal (malleting) of the implant stem, there is a high risk of fracturing the bone, which also increases with the patients' age. (Osteotome systems for implant removal are available from companies such as Exactech Inc and Innomed).

The surgeons' next option is to conduct a vertical osteotomy. This method requires a larger incision along the length of the patient's limb, exposing more of the patient's bone. Once more of the bone is exposed, a vertical cut is made lengthwise along the bone extending through the cortical bone to expose the implant stem fixation. Osteotomes are then inserted into the osteotomy and gently twisted in order to "envelope" (or flex) the site creating a visible gap around the underlying implant. The implant can then be malleted out to break any remaining cement bond. Though proven to be generally effective, this method has some severe drawbacks. Greater bone area exposure and added incision length, can result in complications such as infection. Significant hoop stresses are also generated during the "enveloping" stage of the procedure, creating a high risk of fracture of the contralateral cortex, resulting in longer time in surgery, healing period, and additional probability of complications.

One of the most modern methods of implant extraction utilizes ultrasonic stress energy, and is called ultrasonic cement extraction. (For example, U.S. Pat. No. 5,045,054A can be found at http://www.google.com/patents/US5045054, invented by Hood, Klapper and Caillouette of Advanced Osseous Technologies Inc). Ultrasonic cement extraction devices create a dynamic stress wave centered at the tip of the ultrasonic device, that when placed in the PMMA cement surrounding the implant generates enough heat to essentially melt the cement. Once the PMMA mantle is sufficiently heated, the implant stem can be extracted and assorted hooks and chisels may be used to rid the bone canal of any excess cement. However, because of the extreme heat generated by this approach, a great deal of caution must be exercised to prevent significant bone and tissue damage. The ultrasonic waves should be limited to short pulses, while a constant flow of room temperature fluid (saline solution) should be supplied in order to dissipate heat and cool the surrounding areas. These extra considerations introduce an added degree of complexity, and are still not definitive ways of preventing damage to the bone and surrounding tissue.

Another method that is available is the removal of the implant using a pressurized separating fluid. (U.S. Pat. No. 5,290,291 at http://www.google.com/patents/US5290291 filed by Linden of Hall Surgical, a division of Zimmer Inc.). With this technique, a hole must be drilled into the cement mantle connecting the bone to the implant. The end of this drilled hole must have contact with the implant stem so that the nozzle of a fluid pumping device may be inserted. It is imperative that a seal be formed at the nozzle end, so that the pressurized fluid may be pumped in between the prosthetic and cement mantle. Once the critical pressure of cement failure is reached, the cement should deform, fracture and/or separate, thereby releasing the implant. From here, mechanical energy in addition to the fluid pressure may be applied in the form of striking, or pulling, methods such as those used in other techniques. A benefit to this technique is the lack of heat generation. However, the amount of pressure required to force a fluid into the implant stem-cement interface is large and can lead to rupture of the bone before the critical stress point of the cement is reached.

It should be noted at this point, that the impact methods described above involve the application of external impact forces, which are intended to transfer kinetic energy to the implant. To transfer the kinetic energy efficiently requires rigid stabilization of the patient's limb. However, this is not possible and, in practice, the limb is most often simply held steady by an assistant. As the implant and bone are encased in a significant amount of the patient's soft tissues, the assistant cannot provide rigid stabilization of the limb. Thus, much of the impacted energy is absorbed or dissipated into the patient's soft tissues and assistant's arms. Rather than breaking the implant stem's bond, the stem and bone are displaced, causing soft tissue strains which may lead to nerve damage or other complications.

It would be very advantageous to provide an implant extraction tool for removing a cemented or non-cemented implant stem which avoids the above-mentioned limitations.

SUMMARY

In the present disclosure, a implant extraction tool for removing either cemented or non-cemented intramedullary stem implants from bones is provided and includes An implant extraction tool for removing either cemented or non-cemented intramedullary implant stems from bones, comprising:

a) an elongated handle section having proximal and distal end sections, a cap section affixed to the distal end section of said elongated handle section, said cap section having a hole extending therethrough;

b) an attachment member having opposed ends, one of said opposed ends being configured to grip a cemented or non-cemented intramedullary implant stem in a bone, said attachment member having a size and shape to be received into said hole extending through said cap section, the other of said opposed ends of said attachment member including at least one hook feature; and c) an elongated lever having an elongate proximal section and a shorter distal end section with a pivot fulcrum at a transition from the distal end section to the elongate proximal section, said distal end section being configured to engage the at least one hook feature of the attachment when said proximal end sections of the elongated handle section and the elongated lever are squeezed towards each other such that upon squeezing the proximal end sections together the attachment member is levered out of the hole in the cap section to effect removal of the stem implant.

The tool may further include a mechanical coupling between the proximal end section of the elongated handle section and the elongate proximal section of the elongated lever configured for mechanically forcing the proximal end sections together.

In a non-limiting embodiment, this mechanical coupling may include a mechanical coupling is a screw having a threaded shaft and a handle, and wherein the proximal end section of the elongated handle section and the elongate proximal section of the elongated lever have threaded holes aligned with each other through which the threaded shaft is threaded.

The tool may be a kit including a plurality of interchangeable attachment members, each attachment member in the kit being configured for attachment to a specific stem implant having a known geometry and size.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. The drawings are not scale.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The present disclosure provides a surgical tool for removing a cemented implant stem and is based on a modular handheld lever system with interchangeable attachments that provides a customized grip for the implant to be removed. Thus a purpose of the tool disclosed herein is to be used in orthopedic revision surgery to break implant stems free from their cement mantle.

Figure 1:
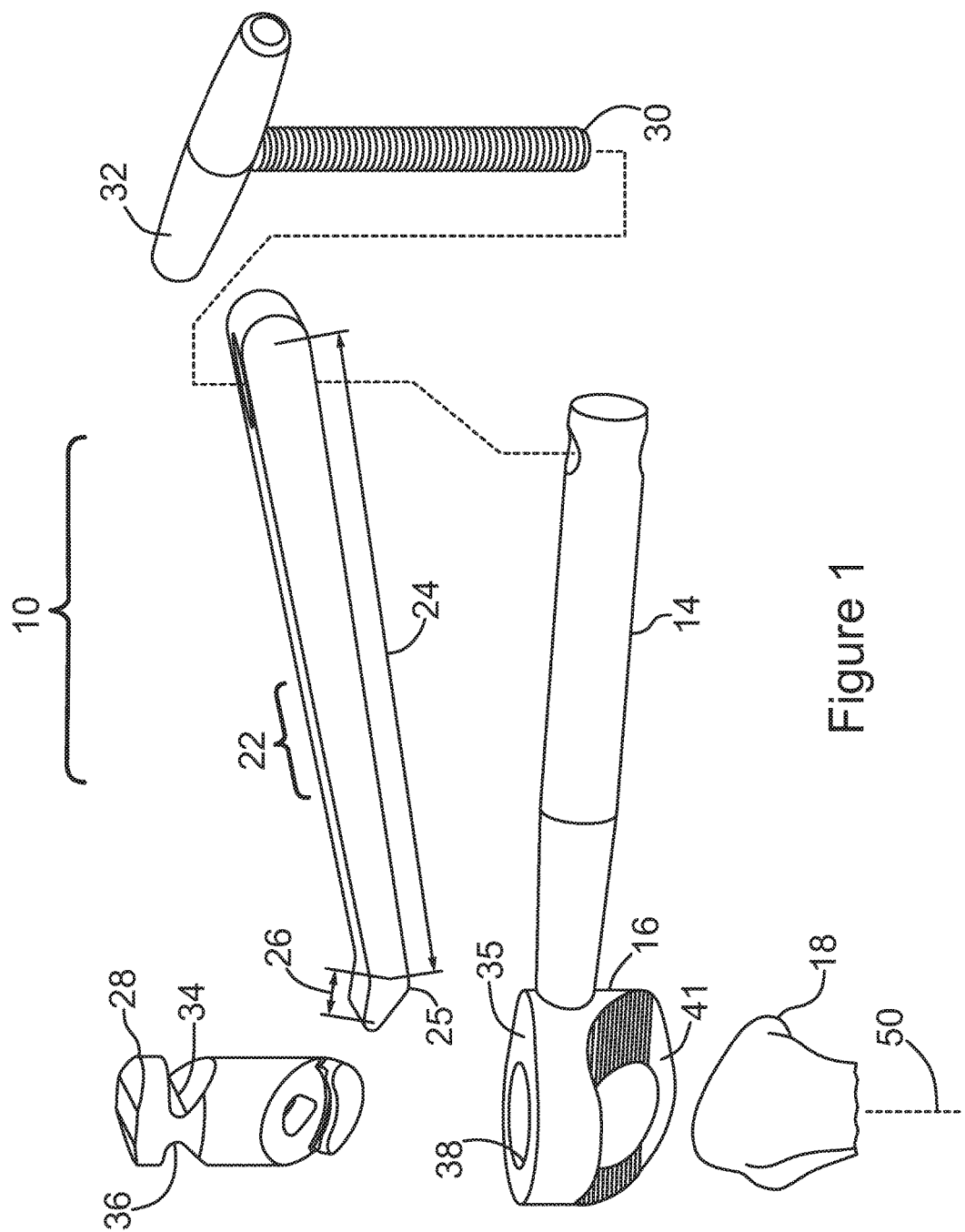
FIG. 1 shows an exploded assembly view of the tool disclosed herein.
Figure 2E:
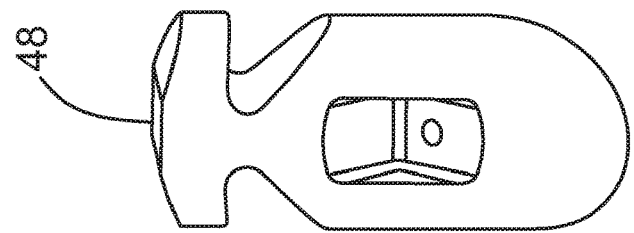
FIGS. 2(a) to (e) show various embodiments of different attachments that may be used forming part of a kit provided with the tool.
Figure 2D:
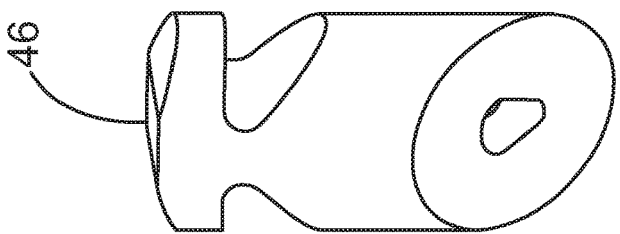
Figure 2C:
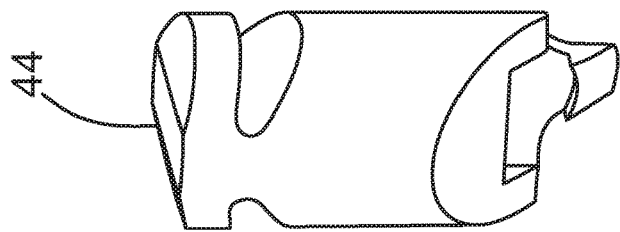
Figure 2B:
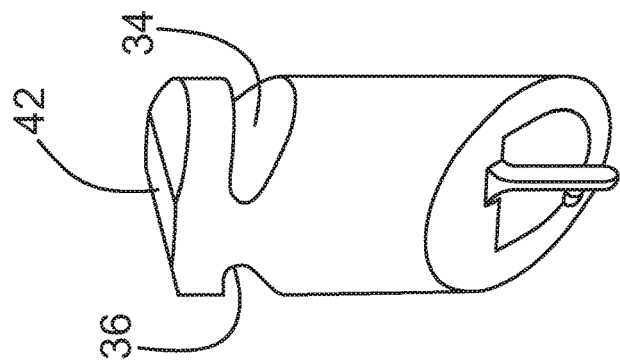
Figure 2A:
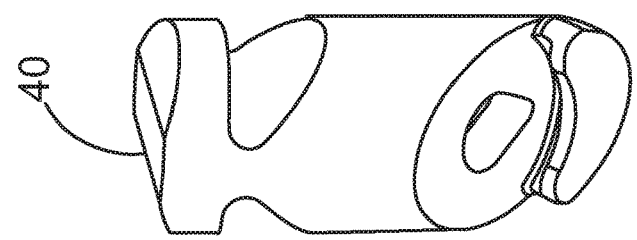

Referring to FIG. 1, the tool, shown generally at 10, includes an elongated handle section 14 having proximal and distal end sections with a cap section 16 attached to the distal end section that sits atop the cut edge of a cut long bone 18 and surrounds the face of the implant, providing a reaction force to the axial vertical force required to remove the implant. Cap section 16 includes a hole 38 to receive therein an attachment 28 described below and a surface 35.

In cases where additional force is required, tool 10 may include an elongated lever 22 having an elongate proximal section 24 and a much shorter distal end section 26 with a pivot fulcrum 25 at the transition from distal end section 24 to the elongate section 26 is used to gain a mechanical advantage when being used, thereby multiplying the surgeon's input force by the ratio of the lengths of the two sections 24 and 26 on either side of the pivot fulcrum 25 of the lever 22.

The attachment 28 that will grip the implant is configured to loosely fit inside the hole 38 in cap section 16 to translate the input force on the lever 22 to a vertical axial force on the implant.

FIGS. 2(*a*) to (*e*) show several embodiments of attachment 28, labelled in FIG. 2 as attachments 40, 42, 44, 46 and 48 respectively that will fit onto most types of implants. Due to the variation of implant geometry and sizes, the tool 10 is designed to accommodate many differently configured attachments 28 to ensure that no matter which implant was used, there will be a suitable attachment to grip and pull it out. Thus, these attachments, such as, but not limited to attachments 40, 42, 44, 46 and 48, are interchangeable in order to be used with the variety of manufactured implants or situations. Attachment 40 is designed to engage the medial edge profile of the Biomet Integrated Shoulder System, or similarly shaped implants. Attachment 42 is designed to engage openings located along the back length of the Stryker Solar shoulder implant and the Tornier Aequalis Fracture Shoulder implant, or similarly shaped implants. Attachment 44 is designed to engage the medial edge profile of the Biomet Integrated Shoulder System, the Tornier Aequalis Fracture Shoulder implant, or similarly shaped implants. Attachments 46 and 48 are designed to engage the thread of the Arthrex Univers II shoulder implant, or similarly shaped implants. It will be appreciated that the various different attachments may be provided as part of a surgical kit along with handle 14, lever 22 and screw 30. When new configurations of implants are designed a corresponding attachment 28 may be made to remove it as well. Each of the attachments 28 in FIG. 1 (same as 40 in FIG. 2) and 42 to 48 all have attachment hooks 34 and 36 on opposite sides of the attachment body configured to be engaged by distal end section 26 of lever 22.

The mechanical advantage can be increased with the use of a lead screw 30 descending through the proximal ends of both the lever 22 and handle 14 (if the force from the lever 22 alone is not sufficient to break the implant out of the cement mantle).

In operation, the surgical exposure is made and the joint is disarticulated to expose the implant's articulation. Using the humeral component of a shoulder replacement implant as an example, refer to FIG. 1 for an exploded view of the tool. The surgeon removes the articular component of the implant, revealing the intramedullary stem. An attachment is selected from the attachments 40, 42, 44, 46 and 48 based on the stem components' design. The selected attachment (40, 42, 44, 46 and 48) is used to engage the stem. Then the handle 14 and cap 16 assembly is slid over the selected attachment until the angled face 41 of cap 16 is securely seated on the exposed bone that was originally cut to install the implant. The distal end section 26 of lever 22 is then positioned with the distal end section 26 resting on surface 35 of cap section 16 and engaged onto one of the attachment's hooks 34 or 36, depending on whether a left or right joint is being operated on. Now the surgeon can apply a manual squeezing force via the handle 14 and the lever 22. The shape of the lever 22 amplifies the squeezing force via the pivot fulcrum 25 and the force is directed axially by the sliding motion created between the attachment 28 and the cap 16. The dimensions of the lever 22 and handle 14 are designed to amplify the grip strength to an axial force level that is matched to the average pullout strength of cemented femoral hip implant stems, plus one standard deviation, in order to facilitate successful separation of any implant stem from its bond. The minimum grip strength required to achieve this separation force is based on the average adult female. This lever 22 and cap 16 design converts the grip strength force to an axial force directed along the longitudinal bone axis 50 shown in FIG. 1 in order to efficiently direct the separation force.

Optionally, the surgeon can employ the lead screw 30 in order to apply the same axial distraction force to the implant, by twisting the lead screw handle 32, (once the threaded portion has been threaded through the threaded sections of lever 22 and handle 14, indicated by the dotted line from the bottom of the threaded section of screw 30) thus squeezing together the proximal ends of handle 14 and lever 22. If these efforts do not release the implant stem, then the optional lead screw 30 can also be used to maintain a constant distraction force while the surgeon strikes the implant with a mallet or uses an osteotome in any traditional manner described in the background section. In this case, the advantage offered by the present extraction tool 10 is that it raises the potential stored energy in the stem-bond interface so that a much less energetic strike is required to break the bond. A less energetic strike means less velocity of a mallet and less risk of unwanted damage or injury. Once the implant is released from the cement fixation or bone fixation bond, then the extraction tool 10 is disassembled in the reverse order and the stem is manually pulled out of the bone. All components of the extraction tool 10 disclosed herein can be made of metals typically used for operating room tools, including but not limited to stainless steel, cobalt chromium, and titanium. All components of the extraction tool 10 disclosed herein can be sanitized using conventional autoclaving and chemical methods for sanitizing operating room tools, and all components can be reused.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An implant extraction tool for removing either cemented or non-cemented intramedullary implant stems from bones, comprising:
   a) an elongated handle section having proximal and distal end sections, a cap section affixed to the distal end section of said elongated handle section, said cap section having a hole extending therethrough and a first surface configured to be seatable on a cut edge of a long bone and a second opposed surface;
   b) an attachment member having opposed ends, one of said opposed ends being configured to grip a cemented or non-cemented intramedullary implant stem in the long bone, said attachment member having a size and shape to be received into said hole extending through said cap section, the other of said opposed ends of said attachment member including at least one hook feature; and
   c) an elongated lever having an elongate proximal section and a shorter distal end section with a pivot fulcrum at a transition from the distal end section to the elongate proximal section, said distal end section being configured to engage said at least one hook feature of said attachment member with the pivot fulcrum resting on the second opposed surface of the cap section, wherein when said proximal end sections of said elongated handle section and said elongated lever are squeezed towards each other, an axial force directed along the longitudinal axis of the long bone is generated by a sliding motion of the attachment member through the hole in the cap section whereby said attachment member is levered out of said hole in said cap section to effect removal of said stem implant.

2. The tool according to claim 1 further comprising a mechanical coupling between said proximal end section of said elongated handle section and said elongate proximal section of said elongated lever configured for mechanically forcing said proximal end sections together.

3. The tool according to claim 2, wherein said mechanical coupling is a screw having a threaded shaft and a handle, and wherein said proximal end section of said elongated handle section and said elongate proximal section of said elongated lever have threaded holes aligned with each other through which said threaded shaft is threaded.

4. The tool according to claim 3, wherein said implant extraction tool includes a plurality of interchangeable attachment members, each attachment member being configured for attachment to a specific stem implant having a known shape, size and geometry.

5. The tool according to claim 2, wherein said implant extraction tool includes a plurality of interchangeable attachment members, each attachment member being configured for attachment to a specific stem implant having a known shape, size and geometry.

6. The tool according to claim 1, wherein said implant extraction tool includes a plurality of interchangeable attachment members, each attachment member being configured for attachment to a specific stem implant having a known shape, size and geometry.

7. An implant extraction tool kit for removing either cemented or non-cemented intramedullary implant stems from bones, comprising
a tool including an elongated handle section having proximal and distal end sections, a cap section affixed to the distal end section of said elongated handle section, said cap section having a hole extending therethrough and a first surface configured to be seatable on a cut edge of a long bone and a second opposed surface;
an attachment member having opposed ends, one of said opposed ends being configured to grip a cemented or non-cemented intramedullary implant stem in the long bone, said attachment member having a size and shape to be received into said hole extending through said cap section, the other of said opposed ends of said attachment member including at least one hook feature; and
an elongated lever having an elongate proximal section and a shorter distal end section with a pivot fulcrum at a transition from the distal end section to the elongate proximal section, said distal end section being configured to engage said at least one hook feature of said attachment member with the pivot fulcrum resting on the second opposed surface of the cap section,
wherein when said proximal end sections of said elongated handle section and said elongated lever are squeezed towards each other, an axial force directed along the longitudinal axis of the long bone is generated by a sliding motion of the attachment member through the hole in the cap section whereby said attachment member is levered out of said hole in said cap section to effect removal of said stem implant; and
a plurality of interchangeable attachment members, each attachment member being configured for attachment to a specific stem implant having a known shape, size and geometry.

8. The kit according to claim 7 wherein said tool further comprises a mechanical coupling between said proximal end section of said elongated handle section and said elongate proximal section of said elongated lever configured for mechanically forcing said proximal end sections together.

9. The kit according to claim 8 wherein said mechanical coupling is a screw having a threaded shaft and a handle, and wherein said proximal end section of said elongated handle section and said elongate proximal section of said elongated lever have threaded holes aligned with each other through which said threaded shaft is threaded.

* * * * *